(12) United States Patent
Bindner et al.

(10) Patent No.: US 7,286,673 B2
(45) Date of Patent: Oct. 23, 2007

(54) EMBEDDED INTERNET FOR HEARING AIDS

(75) Inventors: Joerg Bindner, Weisendorf (DE); Wolfram Meyer, Moehrendorf (DE)

(73) Assignee: Siemens Audiologische Technik GmbH, Erlangen (DE)

( * ) Notice: Subject to any disclaimer, the term of this patent is extended or adjusted under 35 U.S.C. 154(b) by 1024 days.

(21) Appl. No.: 10/342,705

(22) Filed: Jan. 15, 2003

(65) Prior Publication Data
US 2003/0138109 A1    Jul. 24, 2003

(30) Foreign Application Priority Data
Jan. 15, 2002    (DE)    ................ 102 01 323

(51) Int. Cl.
*H04R 25/00* (2006.01)
(52) U.S. Cl. ........................... 381/60; 381/315
(58) Field of Classification Search ................ 381/312, 381/315, 314, 325, 60
See application file for complete search history.

(56) References Cited

U.S. PATENT DOCUMENTS 6,310,556 B1 * 10/2001 Green et al. ........... 340/636.15
6,334,072 B1   12/2001 Leysieffer
7,020,701 B1 *  3/2006 Gelvin et al. ............. 709/224
7,200,237 B2 *  4/2007 Zhang et al. .............. 381/60
2002/0054689 A1 *  5/2002 Zhang et al. ............. 381/312

FOREIGN PATENT DOCUMENTS

| DE | 199 14 993 | 7/2000 |
|----|------------|--------|
| DE | 199 38 318 | 3/2001 |
| WO | WO96/41498 | 12/1996 |
| WO | WO 00/16590 | 3/2000 |

* cited by examiner

*Primary Examiner*—Daniel Swerdlow
(74) *Attorney, Agent, or Firm*—Schiff Hardin LLP

(57) ABSTRACT

A hearing aid has an embedded Internet interface so that the hearing aid can automatically communicate error diagnosis data to a hearing aid acoustician via the Internet so that the hearing aid user need not visit the hearing aid acoustician and so that acoustician can initiate appropriate maintenance, training or repair measures. An appertaining method is also provided.

15 Claims, 1 Drawing Sheet

EMBEDDED INTERNET FOR HEARING AIDS

BACKGROUND OF THE INVENTION

1. Field of the Invention

The present invention is directed to a hearing aid and to a method for the operation of hearing aids in which a quantity relating to an abnormal operating condition(s) is determined and transmitted to an external system. The present invention is particularly directed to the maintenance and operation of hearing aids.

2. Description of the Related Art

Communication between a hearing aid acoustician and a hearing aid normally proceeds via a PC programming device with or without a cable connection. Diagnosing hearing aid faults or adapting the hearing aid is thus limited to the work place of the hearing aid acoustician. One problem with this is that when the customer has left this work place, the hearing aid acoustician usually has no further influence of the proper functioning of this complex device.

Another problem is that the older users who are more likely to be hearing aid wearers are also less attentive in recognizing abnormal conditions of their hearing aid on their own. In such instances, hearing aids are often operated with diminished functionality, which frequently leads to user dissatisfaction.

International Patent Application WO 0016590 A1 discloses such a system for programming hearing aids. This system has a host computer with a communication program for programming the hearing aid. The host computer comprises a first communication interface for sending and receiving control and data signals. A hearing aid programming interface device is connected to the communication interface of the host computer and has a second communication interface for sending and receiving data signals. The first communication interface can be a PCMCIA, USB, RS-232, SCSI or IEEE-1394 interface that is designed for sending and receiving serial data and control signals to and from the hearing aid programming interface device. The first communication interface can likewise be a wireless communication interface that wirelessly exchanges control and data signals with the hearing aid programming interface device.

Additionally, the International Patent Application WO 9641498 A1 discloses a hearing aid that comprises an earpiece that can be completely introduced into the ear canal and that wirelessly communicates with a remote processor unit that amplifies audio signals. The sound of the environment is picked up by a microphone in the earpiece and is sent to the processor unit via a wireless two-way connection together with other information. The wireless connection is set up by microwaves for miniaturizing the components. Over and above this, the wireless connection can also be set up by radar technology.

SUMMARY OF THE INVENTION

The object of the present invention is to provide a hearing aid and a corresponding method with which the diagnosis of hearing aid faults and the adaptation of the hearing aids to individual users can be simplified.

This object is inventively achieved by a method for operating a hearing aid comprising: determining, with the hearing aid, at least one quantity relating to an abnormal operating condition of the hearing aid, and transmitting the determined at least one quantity or a message (which may be based on the quantity) relating to this at least one quantity to an external system with the hearing aid, the external system comprising a data network that is the Internet or other wide-area network, the transmission utilizing an embedded Internet functionality of the hearing aid, and the transmission including an Internet address stored in the hearing aid, More than one internet address may be stored in the hearing aid, and the address may be selected based on the quantity or message. A bidirectional communication mechanism may be provided so that data may be received by the hearing aid from the network. The transmission may ensue wirelessly, and may also include a transmission of the quantity or message (that may be further processed) to a higher-performance transmitter via a short hop transmission; and this may be forwarded to the at least one quantity or message to the data network.

This object is inventively achieved by a hearing aid, comprising: an analysis device configured to determine at least one quantity relating to at least one abnormal operating condition of the hearing aid; a transmission device configured to transmit the determined at least one quantity or a message relating to this at least one quantity to an external system, the external system comprising a data network that is the Internet or other wide-area network, the transmission device comprising: an embedded Internet or wide-area network communication module; and an address register comprising an address to which a respective quantity or message is to be sent. The transmitter may comprise a radio interface, and/or may comprise a receiver configured to receive data. The transmitter may comprise a short hop transmitter having a range of less than one meter. These aspects are described in more detail below.

According to the present invention, it is possible to diagnose hearing aid faults and adapt hearing aids independently of location. This means that the hearing aid user is no longer required to visit the work place of the hearing aid acoustician.

An especially advantageous development is to couple the functionality of a hearing aid with the functionality of the "embedded Internet". Since this separates the communication between the hearing aid and the programming device from location a particular location, the ease in the adaptation of the hearing aid is enhanced and enables a plurality of new functionalities that increase the wearing comfort.

DESCRIPTION OF THE DRAWING

The present invention is explained below in greater detail on the basis of the attached drawing, which is a block diagram showing an inventive system for diagnosing and adapting hearing aids.

DETAILED DESCRIPTION OF THE INVENTION

Figure 1:
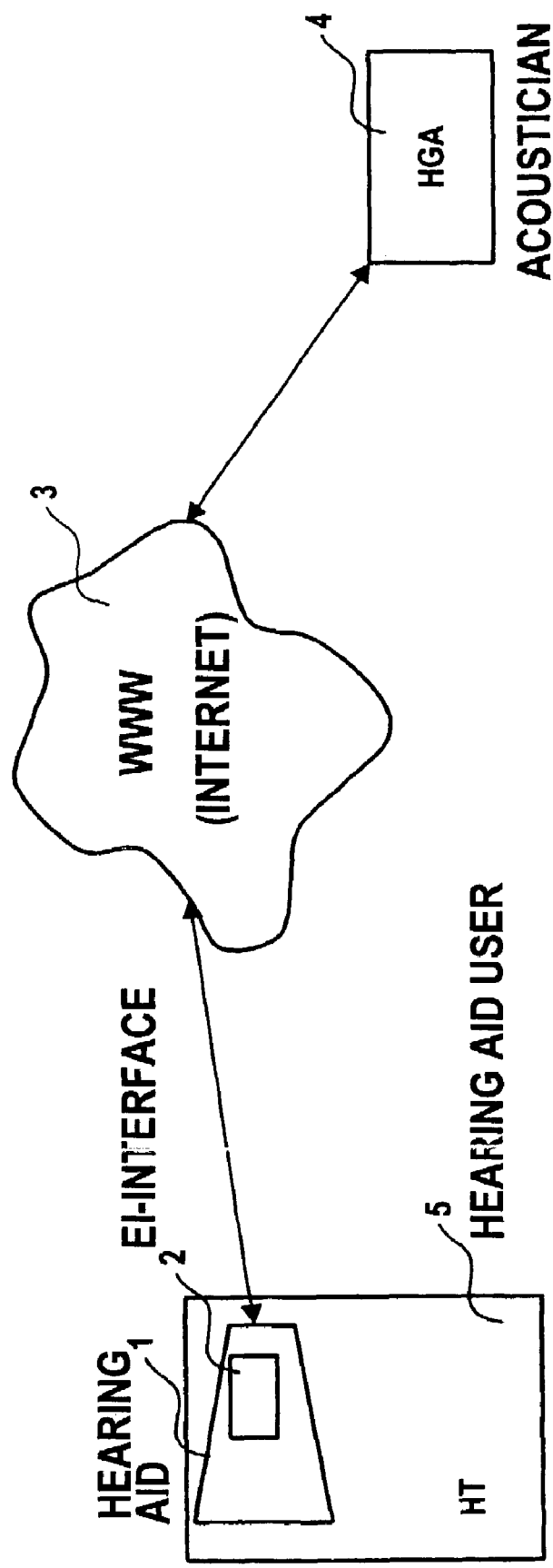

The embodiments described below represent preferred exemplary embodiments of the invention.

The hearing aid 1 shown in the FIGURE comprises an EI (embedded Internet)-interface 2. This EI-interface 2 serves for setting up a bidirectional communication of the hearing aid 1 with the Internet 3. "Embedded Internet" is defined as the use of the Internet for monitoring and controlling factory machinery, communication equipment, data acquisition systems, process control systems, medical-technical equipment, set-top boxes, vehicle controls, office machines, PDAs and other devices. The advantages are low costs, simple user interface and high degree of standardization. Additional information about the Embedded Internet is well known in the art.

The EI-interface 2 has a transmitter and receiver for data exchange with the Internet 3, a memory for storing IP addresses and a circuit for generating corresponding messages. The generated message comprises the IP address of the recipient and the data obtained from or pre-processed by the hearing aid 1. The message is relayed via the Internet 3 to a hearing aid acoustician (HGA) 4 in conformity with the IP address.

The hearing aid acoustician 4 analyzes the received message and potentially sends corresponding data back to the hearing aid 1 using the IP address of the hearing aid 1 that may have been sent to the hearing aid acoustician 4 in the original message. However, the hearing aid acoustician 4 can also make use of other communication mechanisms for the answerback. If the received message makes it necessary, for example, the acoustician 4 could request that the hearing aid user HT 5 visit the acoustician 4 for maintenance measures.

Using the embedded Internet functionality, the hearing aid 1 automatically reports to the hearing aid acoustician 4 that an abnormal condition of the hearing aid 1 itself or of the operating conditions under which the hearing aid 1 works has occurred. Thus, for example, the hearing aid 1 can report to the hearing aid acoustician that the sound canal in the hearing aid 1 is plugged up. The hearing aid acoustician 4 can subsequently initiate appropriate maintenance measures.

Another problem that frequently occurs is that the operator or user 5 of the hearing aid consistently replaces the battery too late; the user 5 just accepts the fact that the device does not work in the desired way. When the hearing aid acoustician 4 receives a message that the battery is low or is being replaced too late, then the hearing aid user 5—if he/she is unaware of this incorrect operation—can receive appropriate training from the hearing aid acoustician 4.

However, the situation can also arise that the hearing aid itself is malfunctioning. For example, the microphone signal can lie beyond the specification. When the hearing aid 1 determines this and informs the hearing aid acoustician 4 via the embedded Internet functionality, then the acoustician 4 can initiate appropriate repair measures.

As previously mentioned, the hearing aid acoustician 4 can transmit data into the hearing aid 1 via the embedded Internet functionality. It is thus possible, for example, to communicate sound specimens to the hearing aid 1 for the adaptation and for a function test without requiring that the hearing aid user 5 be in the presence of the hearing aid acoustician 4. Another application for returning data to the hearing aid 1 would be the transmission of repair datasets so that the hearing aid again works within the specified boundary conditions.

For the purposes of promoting an understanding of the principles of the invention, reference has been made to the preferred embodiments illustrated in the drawings, and specific language has been used to describe these embodiments. However, no limitation of the scope of the invention is intended by this specific language, and the invention should be construed to encompass all embodiments that would normally occur to one of ordinary skill in the art.

The present invention may be described in terms of functional block components and various processing steps. Such functional blocks may be realized by any number of hardware and/or software components configured to perform the specified functions. For example, the present invention may employ various integrated circuit components, e.g., memory elements, processing elements, logic elements, look-up tables, and the like, which may carry out a variety of functions under the control of one or more microprocessors or other control devices. Similarly, where the elements of the present invention are implemented using software programming or software elements the invention may be implemented with any programming or scripting language such as C, C++, Java, assembler, or the like, with the various algorithms being implemented with any combination of data structures, objects, processes, routines or other programming elements. Furthermore, the present invention could employ any number of conventional techniques for electronics configuration, signal processing and/or control, data processing and the like. Use of the term "Internet" is intended to encompass not only the communications description based on present-day standards, but is intended to be broad enough to encompass present-day and future wide-area protocols that would permit the advantages of the invention to be implemented.

The particular implementations shown and described herein are illustrative examples of the invention and are not intended to otherwise limit the scope of the invention in any way. For the sake of brevity, conventional electronics, control systems, software development and other functional aspects of the systems (and components of the individual operating components of the systems) may not be described in detail. Furthermore, the connecting lines, or connectors shown in the various FIGURES presented are intended to represent exemplary functional relationships and/or physical or logical couplings between the various elements. It should be noted that many alternative or additional functional relationships, physical connections or logical connections may be present in a practical device. Moreover, no item or component is essential to the practice of the invention unless the element is specifically described as "essential" or "critical". Numerous modifications and adaptations will be readily apparent to those skilled in this art without departing from the spirit and scope of the present invention.

LIST OF REFERENCE CHARACTERS

1 hearing aid
2 embedded Internet interface
3 Internet
4 hearing aid acoustician
5 hearing aid user

What is claimed is:

1. A method for operating a hearing aid comprising:
   determining, with the hearing aid, a status of a battery of the hearing aid;
   transmitting the status of the battery or a message relating to this status to an external system with the hearing aid, the external system comprising a data network that is the Internet or other wide-area network, the transmission utilizing an embedded Internet functionality of the hearing aid, and the transmission including an Internet address stored in the hearing aid;
   changing the battery of the hearing aid by a hearing aid user;
   determining, with the external system, whether the battery was changed too late; and
   training the hearing aid user to appropriately change the battery.

2. The method according to claim 1, further comprising:
   providing more than one Internet address that is stored in the hearing aid; and
   providing an internet address for transmitting.

3. The method according to claim 1, further comprising:
providing a bidirectional communication between the hearing aid and the data network; and
receiving data by the hearing aid from the data network.

4. The method according to claim 1, wherein the transmitting ensues wirelessly.

5. The method according to claim 1, further comprising:
generating a message to be transmitted based on the battery status.

6. The method according to claim 1, the step of transmitting further comprising:
transmitting the battery status to a higher-performance transmitter via a short hop transmission; and
forwarding the battery status to the data network.

7. The method according to claim 6, further comprising:
further processing the battery status before the forwarding.

8. The method according to claim 1, wherein determining whether the battery was changed too late comprises determining if the battery is low.

9. A hearing aid, comprising:
an analysis device configured to determine whether a battery of the hearing aid is changed too late, and to generate corresponding information data;
a transmission device configured to transmit the information data to an external system, the external system comprising a data network that is the Internet or other wide-area network, the transmission device comprising:
an embedded Internet or wide-area network communication module; and
an address register comprising an address to which a respective information data is to be sent.

10. The hearing aid according to claim 9, wherein the transmission device is a transmitter/receiver device that comprises a receiver configured to receive data.

11. The hearing aid according to claim 9, wherein the transmission device comprises a radio interface.

12. The hearing aid according to claim 9 comprising a message generator configured to generate a message based on the battery status.

13. The hearing aid according to claim 9, wherein the transmission device comprises a short hop transmitter having a range of less than one meter.

14. A method for operating a hearing aid, comprising:
changing a battery of the hearing bid by the hearing aid user;
determining, with the hearing aid, whether the battery of the hearing aid was changed too late and generating corresponding Information data,
transmitting the information data to an external system with the hearing aid, the external system comprising a data network that is the Internet or other wide-area network, the transmission utilizing an embedded Internet functionality of the hearing aid, and the transmission including an Internet address stored in the hearing aid; and
training of the hearing aid user to appropriately change the battery on the basis of the information data received by the external system.

15. A training system for training a hearing aid user, comprising:
a hearing aid according to claim 9, which sends information data whether a battery of the hearing aid was changed too late to a training unit; and
said training unit being configured to perform a training of the hearing aid user to appropriately change the battery.

* * * * *